US006780413B2

(12) United States Patent
Hott et al.

(10) Patent No.: US 6,780,413 B2
(45) Date of Patent: Aug. 24, 2004

(54) IMMUNOTOXIN (MAB-RICIN) FOR THE TREATMENT OF FOCAL MOVEMENT DISORDERS

(75) Inventors: Jonathan S. Hott, Birmingham, MI (US); Richard J. Youle, Bethesda, MD (US); Mark Hallett, Bethesda, MD (US); Marinos C. Dalakas, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 50 days.

(21) Appl. No.: 10/005,512

(22) Filed: Nov. 7, 2001

(65) Prior Publication Data

US 2002/0081303 A1 Jun. 27, 2002

Related U.S. Application Data

(63) Continuation of application No. 09/418,854, filed on Oct. 15, 1999, now abandoned, which is a continuation of application No. 08/937,266, filed on Sep. 15, 1997, now abandoned.
(60) Provisional application No. 60/027,458, filed on Sep. 19, 1996.

(51) Int. Cl.[7] .......................................... A61K 39/395
(52) U.S. Cl. .................................. 424/143.1; 424/183.1
(58) Field of Search ....................................... 424/183.1

(56) References Cited

U.S. PATENT DOCUMENTS

| 5,183,462 A | 2/1993 | Borodic ........................ 604/51 |
| 5,239,062 A | 8/1993 | Blattler et al. ............... 530/396 |
| 5,562,907 A | 10/1996 | Arnon ....................... 424/236.1 |
| 5,721,215 A | 2/1998 | Aoki et al. .................... 514/21 |

FOREIGN PATENT DOCUMENTS

EP    0 770 395 A1    2/1997    .......... A61K/38/16

OTHER PUBLICATIONS

Appel, S.H. et al., "Accelerated degradation of acetylcholine receptor from cultured rat myotubes with myasthenia gravis sera and globulins," Proc Natl Acad Sci U S A. May 1977;74(5):2130–4.
Barbet, J. et al., "Specific Toxicity to Activated T and B Lymphocytes of a Ricin A Immunotoxin Directed Against the Class 1 MHC Antigen H–2 K" Antibody, Immunoconj. Radiopharmaceuticals 1(2):169–180 (1988).
Borodic, G. et al., "Botulinum toxin therapy, immunologic resistance, and problems with available materials," Neurology. Jan. 1996;46(1):26–9.
Christiansen, S.P. et al., "Acute effects of the skeletal muscle–specific immunotoxin ricin–mAb 35 on extraocular muscles of rabbits," Invest Ophthalmol Vis Sci. Oct. 2000;41(11):3402–9.

Clementi, F. et al., "Acetylcholine receptor degradation: study of mechanism of action of inhibitory drugs " Eur J Cell Biol. Jan. 1983;29(2):274–80.
Clementi, F. et al., "Antibody induced internalization of acetylcholine nicotinic receptor: kinetics, mechanism and selectivity," Eur J Cell Biol. May 1985;37:220–8.
de la Cruz, R.R. et al., "Behavior of cat abducens motoneurons following the injection of toxic ricin into the lateral rectus muscle," Brain Res. Mar. 29, 1991;544(2):260–8.
de la Cruz, R.R. et al., "Effects of target depletion on adult mammalian central neurons: functional correleates," Neuroscience. Jan 1994;58(1):81–97.
de la Cruz, R.R. et al., "Neurotoxic lesion of oculomotor neruons: evidence for rearrangement of axon terminals of surviving afferent neurons," Neurotoxicology. 1994 Fall;15(3):633–6.
de al Cruz, R.R. et al., "Response of adult cat abducens internuclear interneurons to selective removal of their target motoneurons," Exp Brain Res. 1991;84(1):167–72.
Gardner, J.M. et al., "Acetylcholine receptor degradation measured by density labeling: effects of cholingeric ligands and evidence against recycling," Cell. Mar. 1979;16(3):661–74.
Goldmacher, V.S. et al., "The specific cytotoxicity of immunoconjugates containing blocked ricin is dependent on the residual binding capacity of blocked ricin: evidence that the membrane binding and A–chain translocation activities of ricin cannot be speparated," Biochem Biophys Res Commun.Mar. 16, 1992;183(2):758–66.
Greenfield, L. et al., "Mutations in diphtheria toxin separate binding from entry and amplify immunotoxin selectivity," Science. Oct. 23, 1987;238(4826):536–9.
Griffin, T.W. et al., "Chimeras, Castor Beans and Cancer: Antibody and Ligand–Toxin Conjugates as Therapeutic Agents," In: Cancer Therapy in the Twenty–First Century: Molecular and Immunologic Approaches, Futura Publishing Co., Inc., Mt. Kisco, NY 1994.
Grossband, M.L. et al., "Correlation between in vivo toxicity and preclinical in vitro parameters for the immunotoxin anti–B4–blocked ricin," Cancer Res. Aug. 1, 1992;52(15):4200–7.
Holds, John B. et al., "Botulinum A toxin injection. Failures in clinical practice and a biochemical system for the study of toxin–induced paralysis," Ophthal Plast Reconstr Surg. 1990;6(4):252–9.
Leonard, J.E. et al., "Kinetics of protein synthesis inactivation in human T–lymphocytes by selective monoclonal antibody–ricin conjugates," Cancer Res. Nov. 1985;45(11 Pt 1):5263–9.

(List continued on next page.)

Primary Examiner—Patrick J. Nolan
(74) Attorney, Agent, or Firm—Jeffrey I. Auerbach; Liniak, Berenato & White, LLC

(57) ABSTRACT

Compositions and methods for treatment of focal muscle spasms. Immunotoxin conjugates comprise a toxin conjugated to an antibody reactive to a muscle specific antigen.

11 Claims, 2 Drawing Sheets

OTHER PUBLICATIONS

Loutrari, H. et al., "Use of Torpedo–mouse hybrid acetylcholine receptors reveals immunodominance of the alpha subunit in myasthenia gravis antisera," Eur J Immunol. Nov. 1992;22(11):2949–56.

Moreno–Lopez, B. et al., "Botulinum neurotoxin alters the discharge characteristics of abducens motoneurons in the alert car," J Neurophysiol. Oct. 1994;72(4):2041–4.

Printseva, O. et al., "Selective killing of smooth muscle cells in culture by the ricin A–chain conjugated with monoclonal antibodies to a cell surface antigen via a dextran bridge," Expericentia Oct. 15, 1985;41(10):1342–4.

Vitetta, E.S. et al. "Synergy of ricin A chain–containing immunotoxins and ricin B chain–containing immunotoxins in in vitro killing of neoplastic human B cells," Proc Natl Acad Sci U S A. Oct. 1983;80(20):6332–5.

Weil–Hillman, G. et al., "Combined immunochemotherapy of human solid tumors in nude mice," Cancer Res. Jan. 15, 1987;47(2):579–85.

Weil–Hillman. G. et al., "Cytotoxic effect of anti–Mr 67,000 protein immunotoxins on human tumors in a nude mouse model," Cancer Res. Mar. 1985;45(3):1328–36.

Wiley, R.G., "Neural lesioning with ribosome–inactivating proteins: suicide transport and immunolesioning" Trends Neurosci. Aug. 1992;15(8):285–90.

Youle, R.J. et al., "Role of Endocytosis and Receptor Recycling in Ligang–Toxin and Antibody–Toxin Conjugate Activity," In: Immunoconjugates. Antibody Conjugates in Radioimaging and Therapy of Cancer (C.–W. Vogel, Ed.) New York, Oxford Univerisity Press, pp. 153–169.

Youle R.J. et al., "Studies on the galactose–binding site of ricin and the hybrid toxin Man6P–ricin," Cell. Feb. 1981;23(2):551–9.

IMMUNOTOXIN (MAB-RICIN) FOR THE TREATMENT OF FOCAL MOVEMENT DISORDERS

CROSS-REFERENCE TO RELATED APPLICATIONS

This application is a continuation of U.S. patent application Ser. No. 09/418,854 (filed: Oct. 15, 1999, now abandoned), which is a continuation of U.S. patent application Ser. No. 08/937,266 (filed: Sep. 15, 1997, now abandoned), which claims the benefit of U.S. patent application Ser. No. 60/027,458 (filed Sep. 19, 1996).

TECHNICAL FIELD

Compositions comprising a toxin conjugated to an antibody selectively reactive to a muscle specific antigen. Methods of using the immunotoxin conjugates for treatment of focal muscle spasms are also provided.

BACKGROUND OF THE INVENTION

A variety of neurological disorders are characterized by disabling, involuntary muscular spasms. The most successful treatment for focal muscle spasm is intramuscular injection of the botulinum toxin A (BTX), the only pharmaceutical formulation of botulinum toxin currently on the market. Intramuscular injection of BTX weakens the muscles and reduces the symptoms. (Jankovic and Brin, *N. Engl. J. Med.*, (1991) 324:1186–1194; Stell and Moore, History and current applications of botulinum toxin treatment. In: Moore P, ed. Handbook of botulinum toxin treatment. Oxford: Blackwell Science, Inc., 1995:3–15; Report of the Therapeutics and Technology Assessment Subcommittee of the American Academy of Neurology. Assessment: the clinical usefulness of botulinum toxin-a in treating neurologic disorders. *Neurology* (1990) 40:1332–1336; Coffield et a. The site and mechanism of action of botulinum neurotoxin. In: Jankovic J, Hallett M, eds. Therapy with botulinum toxin. New York: Marcel Dekker, Inc., (1994) 3–14). However, the therapeutic effect of BTX is transient and as the BTX paralytic effects wane, patients usually receive additional injections. For many patients, repeated exposure to BTX has been accompanied with decreasing efficacy and duration of benefit. Collateral sprouts of denervated motor nerve terminals and increasing titers of toxin neutralizing antibodies are two mechanisms of resistance to BTX (Coffield et al., supra, Jankovic and Schwartz, *Neurology* (1995) 45:1743–1746). As a result, larger and more frequent doses of BTX become necessary for relief of the spasm, increasing the risk of side-effects. Eventually, some patients become completely refractory to treatment.

Accordingly, what is needed in the art is a means to treat focal muscle disorders with greater specificity and duration of effect. The present invention provides these and other advantages.

SUMMARY OF THE INVENTION

In one aspect the present invention is directed to a method of treating a focal muscle spasm. The method comprises the steps of administering, by intramuscular injection, a therapeutically effective dose of an immunotoxin conjugate to a muscle of the focal muscle spasm. The immunotoxin conjugate comprises an antibody conjugated to a toxin selected from the group consisting of: ricin and abrin, and the antibody is selectively reactive, under immunologically reactive conditions, to a nicotinic acetylcholine receptor (nAchR). In preferred embodiments the antibody is a monoclonal antibody. Typically, the mammalian acetylcholine receptor is a human acetylcholine receptor. In particularly preferred embodiments the toxin is ricin. Typically the focal muscle spasm is selected from the group consisting of: blepharospasm, cervical dystonia, hand dystonia, limb dystonia, hemifacial spasm, bruxism, strabismus, VI nerve palsy, spasmodic dysphonia, and oromandibular dystonia. In other embodiments a therapeutically effective amount of the immunotoxin conjugate is administered with a therapeutically effective amount of botulinum toxin, as an immunoconjugate or in unconjugated form.

In another aspect the present invention relates to a method of treating a focal muscle spasm. The method comprises the steps of administering, by intramuscular injection, a therapeutically effective dose of an immunotoxin conjugate to a muscle of the focal muscle spasm. The immunotoxin conjugate comprises an antibody conjugated to a galactose binding moiety and a toxin selected from the group consisting of: ricin-A and abrin-A, and the antibody is selectively reactive, under immunologically reactive conditions, to a nicotinic acetylcholine receptor (nAchR). In some embodiments the galactose binding moiety is selected from the group consisting of: ricin-B and abrin-B. In preferred embodiments the antibody is a monoclonal antibody. Typically, the mammalian acetylcholine receptor is a human acetylcholine receptor. In particularly preferred embodiments the toxin is ricin. Typically the focal muscle spasm is selected from the group consisting of: blepharospasm, cervical dystonia, hand dystonia, limb dystonia, hemifacial spasm, bruxism, strabismus, VI nerve palsy, spasmodic dysphonia, and oromandibular dystonia.

In another aspect the present invention relates to an immunotoxin conjugate, comprising an antibody conjugated to a toxin selected from the group consisting of: ricin and abrin, where the antibody is selectively reactive, under immunologically reactive conditions, to a mammalian nicotinic acetylcholine receptor. In preferred embodiments the antibody is a monoclonal antibody. Typically, the mammalian acetylcholine receptor is a human acetylcholine receptor. In particularly preferred embodiments the toxin is ricin.

BRIEF DESCRIPTION OF THE DRAWINGS

FIG. 1 shows the effects of unilateral infusion of either BTX at $\frac{1}{100}$ of the $LD_{50}$ or ITX at $\frac{1}{100}$ of the maximum tolerated dose (MTD) into the gastrocnemius muscle of female Sprague-Dawley rats compared to control (PBS) injected rats on rotorod performance. Data points were recorded as time spent on the rotorod before the first fall. The average time on the rotorod for three consecutive runs per rat was used as the score for each rat. Data points represent the average of the individual scores by rats within each group. Vertical lines indicate the standard deviation (n=6).

FIG. 2 shows the effects of different doses of either BTX or ITX injected into the gastrocnemius muscle on rotorod performance. Two control groups were utilized, PBS and unconjugated anti-nicotinic AchR MoAb 35. The doses of BTX-$\frac{1}{10}$ and $\frac{1}{100}$ of the $LD_{50}$-were chosen based on the range of doses used for treatment of humans. BTX was compared to ITX at doses $\frac{1}{100}$ and $\frac{1}{300}$ of the maximum tolerated dose (MTD). Standard deviation of the mean was calculated as described in FIG. 1, except 4 rats were used in each experimental group.

DETAILED DESCRIPTION OF THE INVENTION

Intramuscular injection of botulinum toxin A (BTX) is often considered primary therapy of many disorders characterized by muscular spasms. The utility of BTX, however, is limited by its short duration of action, the possible development of resistance after repeated injections, and cross-reactivity with autonomic neurons. Surprisingly, we have determined an immunotoxin (ITX) engineered to damage skeletal muscle fibers selectively by chemically linking a monoclonal antibody against the nicotinic acetylcholine receptor to the toxin ricin was 20,000-fold more toxic to myotubes than myoblasts, consistent with the degree of acetylcholine receptor expression. In vivo, ITX produced destructive myopathic changes at a dose 300-fold less than the maximum tolerated dose. Assessment of rat muscle strength after unilateral gastrocnemius injections showed ITX was more effective and had a longer duration of action than BTX. Immunotoxins of the present invention have utility as a tissue culture selection agent against cells or tissues expressing nicotinic acetylcholine receptors (nAchR) Immunotoxins of the present invention also have utility in the treatment of involuntary muscle spasms. Patients repeatedly exposed to botulinum toxin for the treatment of muscle spasms frequently become resistant to its use. Consequently, surgical treatment is often indicated. Intramuscular injection of the immunotoxin conjugates of the present invention can delay or prevent the requirement for surgery.

Definition

Units, prefixes, and symbols can be denoted in their SI accepted form. Numeric ranges are inclusive of the numbers defining the range. The headings provided herein are not limitations of the various aspects or embodiments of the invention which can be had by reference to the specification as a whole. Accordingly, the terms defined immediately below are more fully defined by reference to the specification as a whole.

The terms "immunotoxin conjugate" or "immunotoxin" include reference to a covalent or non-covalent linkage of a toxin to an antibody. The toxin may be linked directly to the antibody, or indirectly through, for example, a linker molecule.

The term "antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). An antibody immunologically reactive with a particular antigen can be generated in vivo or by recombinant methods such as selection of libraries of recombinant antibodies in phage or similar vectors. See, e.g., Huse et al (1989) *Science* 246:1275–1281; and Ward, et al. (1989) *Nature* 341:544–546; and Vaughan et al. (1996) *Nature Biotechnology*, 14:309–314.

The term "humanized antibody" includes reference to an antibody which comprises a non-human amino acid sequence but whose constant region has been altered to reduce immunogenicity in humans.

The term "conjugated" includes reference to a covalent or non-covalent linkage. The linkage may be direct or indirect via an intermediary molecule.

The term "ricin" includes reference to the lectin $RCA_{60}$ from *Ricinus communis* (Castor bean). The term also references toxic variants thereof. See, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65,000 and 120,000, respectively. Nicholson and Blaustein, *J. Biochim. Biophys. Acta,* 266:543 (1972). $RCA_{60}$, also referred to as $RCA_{II}$, Ricin D or RCL III is extremely toxic, inhibits protein synthesis and has an affinity for N-acetyl-D-galactosamine. The toxin is a dimer of an A-chain (30,000 Da) and B-chain (33,000 Da) joined by a disulfide bond. The A chain is responsible for inactivating protein synthesis and killing cells. The B chain binds ricin to cell-surface galactose residues and facilitates transport of the A chain into the cytosol (Olsnes et al., *Nature,* 1974;249:627–631). See, U.S. Pat. No. 3,060,165.

The term "abrin" includes reference to the toxic lectins from *Abrus precatorius*. The toxic principles, abrin a, b, c, and d, have a molecular weight of from about 63,000 and 67,000 Da and are composed of two disulfide-linked polypeptide chains A and B. The A chain inhibits protein synthesis; the B-chain (abrin-b) binds to D-galactose residues. See, Funatsu et a/, The amino acid sequence of the A-chain of abrin-a and comparison with ricin, *Agr. Biol. Chem.* 52:1095 (1988). See also, Olsnes, *Methods Enzymol.* 50:330–335 (1978).

The term "selectively reactive" includes reference to the preferential association of a ligand, in whole or part, with a cell or tissue bearing a particular target molecule or marker and not to cells or tissues lacking that target molecule. It is, of course, recognized that a certain degree of nonspecific interaction may occur between a molecule and a non-target cell or tissue. Nevertheless, specific binding, may be distinguished as mediated through specific recognition of the target molecule. Typically specific binding results in a much stronger association between the delivered molecule and cells bearing the target molecule than between the bound molecule and cells lacking the target molecule. Specific binding typically results in greater than 2 fold, preferably greater than 5 fold, more preferably greater than 10 fold and most preferably greater than 100 fold increase in amount of bound ligand (per unit time) to a cell or tissue bearing the target molecule as compared to a cell or tissue lacking the target molecule or marker. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols. See Harlow and Lane (1988) *Antibodies, A Laboratory Manual*, Cold Spring Harbor Publications, New York, for a description of immunoassay formats and conditions. Preferably, immunologically reactive conditions are "physiological conditions" which includes reference to conditions (e.g., temperature, osmolarity, pH) that are typical inside a living mammal or a mammalian cell. While it is recognized that some organs are subject to extreme conditions, the intra-organismal and intra-cellular environment normally varies around pH 7 (i.e.

from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The terms "mammalian nicotinic acetylcholine receptor" or "nAchR" include reference to peripheral, ligand-gated ion channel which is present on "fast" and "slow" muscles and located at the post-synaptic membrane of the neuromuscular junction (motor end plate). Mammalian nicotinic acetylcholine receptors are typically from primates, preferably from humans.

The term "focal muscle spasm" includes reference to a brief, unsustained contraction, or a paroxysmal, spontaneous, prolonged contraction of one or more muscles. The term references those focal muscle spasms, the therapeutic treatment of which comprises selective destruction of one or more muscles at the site of the focal muscle spasm. Typical focal muscle spasms include blepharospasm, cervical dystonia, hand dystonia, limb dystonia, hemifacial spasm, bruxism, strabismus, VI nerve palsy, spasmodic dysphonia, and oromandibular dystonia. See, Brooke, M. H., A Clinician's View of Neuromuscular Diseases. Baltimore, Williams & Wilkins, 1986; and Layzer, R. B., Muscle pain, cramps and fatigue, in Myology, AG Engel, BQ Banker (eds.). New York, McGraw-Hill, 1986.

The term "galactose binding moiety" includes reference to composition which selectively reacts with cell surface galactose residues. Typically, the galactose binding moiety is an antibody, lectin, or lectin derivative (e.g., a subunit thereof). Preferred lectins or derivatives thereof include: abrin (e.g., abrin-b), ricin (e.g., ricin-b). Particularly preferred are ricin-b and abrin-b.

The terms "effective amount" or "amount effective to" or "therapeutically effective amount" includes reference to a dosage sufficient to produce a desired result. Typically, the desired result is reduction in the severity of a focal muscle spasm.

Antibodies to Muscle Specific Antigens

Antibodies of the present invention are selectively reactive, under immunologically reactive conditions, to a muscle specific antigen. The term "muscle specific antigen" includes reference to those antigens whose presence is substantially limited to the membrane of muscle cells at the localized site at which the immunotoxin of the present invention is administered. Thus a muscle specific antigen may be present on non-muscle cells but is substantially inaccessible to the immunotoxins of the present invention due to the mode of administration. Preferably, however, muscle specific antigens are unique to muscle cells.

Muscle specific antigens are known in the art. For example, antibodies reactive to N-CAM (neuronal cell adhesion molecule) can and have been generated and are available commercially (Sigma Chemical Company, St. Louis, Mo.). Anti-N-CAM monoclonals bind to the CD56 differentiation antigen specifically expressed on regenerating or newly denervated muscle fibers (Couvalt and Sanes, *Proc. Natl. Acad. Sci. USA* (1985) 82:4544–4548; Cashman et al., *Ann. Neurol.* (1987) 21:481–489; IIIa I, Leon-Monzon M, Dalakas M C., *Ann. Neurol.* 1992; 31:46–52). Likewise, the muscle-specific antigen Leu-19 (Becton Dickinson) can be used to generate antibodies by standard immunological methods. Antibodies to other muscle specific antigens, such as monoclonal anti-dystrophin, are commercially available (Sigma).

In preferred embodiments the muscle specific antigen is a nicotinic acetylcholine receptor (nAchR). The nAch receptor and antibodies generated thereto are readily available from publicly accessible depositories. Cell line TE671 (equivalent to the RD cell line) expresses AchR for preparation of anti-human nAchR antibodies and is available from the ATCC under deposit number CRL 8805. See, U.S. Pat. Nos. 5,041,389, and 4,789,640, both incorporated herein by reference. Hybridomas producing a human IgG1 monoclonal antibody against nAchR is deposited with the Fermentation Research Institute of Japan under the accession number FERM BP-1798 (U.S. Pat. No. 5,192,684, incorporated herein by reference). Monoclonal antibodies to acetylcholine receptors are produced by hybridomas having accession number ATCC Nos.: HB 8987 (mAb 64), HB 189 (mAb 270), and TIB 175 (mAb 35), all of which are incorporated herein by reference.

Many methods of making antibodies are known to persons of ordinary skill. "Antibody" includes antigen binding forms of antibodies (e.g., Fab, $F(ab)_2$). The term also refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The following discussion is presented as a general overview of the techniques available; however, one of skill will recognize that many variations of the following methods are known.

A. Antibody Production

A number of immunogens are used to produce antibodies specifically reactive with a muscle specific antigen. A recombinant, synthetic, or native muscle specific antigen of 5 contiguous amino acids in length or greater from a muscle specific antigen is the preferred immunogen (antigen) for the production of monoclonal or polyclonal antibodies. The term "recombinant" when used with reference to a cell, or nucleic acid, or vector, includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

In a typical procedure, the muscle specific antigen is injected into an animal capable of producing antibodies. Methods of producing polyclonal antibodies are known to those of skill in the art. In brief, an immunogen (antigen), preferably a purified muscle specific antigen (e.g., nAchR), an muscle specific antigen coupled to an appropriate carrier (e.g., GST, keyhole limpet hemanocyanin, etc.), or an muscle specific antigen incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the muscle specific antigen of interest. When appropriately high titers of antibody to the immunogen are obtained, blood is collected from the animal and antisera are prepared. Further fractionation of the antisera to enrich for antibodies reactive to the muscle specific antigen is performed where desired (see, e.g., Coligan (1991) *Current Protocols in Immunology* Wiley/Greene, NY; and Harlow and Lane (1989) *Antibodies: A Laboratory Manual* Cold Spring Harbor Press, N.Y.).

Antibodies, including binding fragments and single chain recombinant versions thereof, against predetermined fragments of muscle specific antigen are raised by immunizing animals, e.g., with conjugates of the fragments with carrier proteins as described above. Typically, the immunogen of interest is an muscle specific antigen of at least about 5 amino acids, more typically the muscle specific antigen is 10 amino acids in length, preferably, 15 amino acids in length and more preferably the muscle specific antigen is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to an muscle specific antigen from which the immunogen was derived. Specific monoclonal and polyclonal antibodies will usually bind with a $K_D$ of at least about 0.1 mM, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen comprising an muscle specific antigen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transfection with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The muscle specific antigens and antibodies of the present invention are used with or without modification, and include chimeric antibodies such as humanized murine antibodies.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996).

Also, recombinant immunoglobulins may be produced. See, Cabilly, U.S. Pat. No. 4,816,567; and Queen et al. (1989) *Proc. Nat'l Acad. Sci. USA* 86: 10029–10033.

B. Human or Humanized (Chimeric) Antibody Production

The anti-muscle specific antigen antibodies of this invention can also be administered to a mammal (e.g., a human patient) for therapeutic purposes (e.g., as targeting molecules when conjugated or fused to effector molecules such as labels, cytotoxins, enzymes, growth factors, drugs, etc.). Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

i) Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

ii) Human Antibodies

In another embodiment, this invention provides for fully human anti-muscle specific antigen antibodies. Human antibodies consist entirely of characteristically human polypeptide sequences. The human anti-muscle specific antigen antibodies of this invention can be produced in using a wide variety of methods (see, e.g., Larrick et al, U.S. Pat. No. 5,001,065, for review).

In preferred embodiments, the human anti-muscle specific antigen antibodies of the present invention are usually produced initially in trioma cells. Genes encoding the antibodies are then cloned and expressed in other cells, particularly, nonhuman mammalian cells. The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual*, 2nd ed., Cold Spring Harbor, N.Y., 1989; Berger & Kimmel, *Methods in Enzymology*, Vol. 152: *Guide to Molecular Cloning Techniques*, Academic Press, Inc., San Diego, Calif., 1987; Co et al. (1992) *J. Immunol.*, 148: 1149). For example, genes encoding heavy and light chains are cloned from a trioma's genomic DNA or cDNA produced by reverse transcription of the trioma's RNA. Cloning is accomplished by conventional techniques including the use of PCR primers that hybridize to the sequences flanking or overlapping the genes, or segments of genes, to be cloned.

Formation of Immunotoxic Conjugates

Antibodies specifically reactive to muscle specific antigens are joined via covalent or non-covalent bond to a toxin selected from the group comprising: ricin, abrin, ricin-a, abrin-a, and botulinum toxin. Ricin, abrin, and subunits thereof as well as botulinum toxin A through F, are readily available from commercial sources (e.g, Sigma Chemical Company, St. Louis, Mo.). Methods of isolating ricin and abrin are also well known to those of ordinary skill in the art. See, e.g., Nicholson and Blaustein, *J. Biochim. Biophys. Acta,* 266:543 (1972); Tomita et al., *Experientia,* 28:84 (1972); Wei et al., *J. Biol. Chem.,* 249:3061 (1974); Lin et al. *Toxicon.,* 19:41 (1981); Olsnes et al. *J. Biol. Chem.* 249:803 (1974); Wei et al., *J. Mol. Biol.,* 123:707 (1978); Lin and Li, *Eur. J. Biochem.,* 105:453 (1980); Nicolson et al. *Biochemistry,* 13:196 (1974); and, Olsnes, *Methods Enzymol.* 50:330–335 (1978), all of which are incorporated herein by reference. The molecules may be attached by any of a number of means well-known to those of skill in the art. In some embodiments, the immunotoxic conjugates of the present invention are recombinantly expressed as single-chain fusion protein comprising both antibody and toxin. Typically the toxin will be conjugated, either directly or through a linker (spacer), to the ligand.

A "linker", as used herein, is a molecule that is used to join two molecules. The linker is capable of forming covalent bonds or high-affinity non-covalent bonds to both molecules. Suitable linkers are well known to those of ordinary skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine).

The procedure for attaching a toxin to an antibody or other polypeptide targeting molecule will vary according to the chemical structure of the toxin. Antibodies contain a variety of functional groups; e.g., sulfhydryl (—S), carboxylic acid (COOH) or free amine (—$NH_2$) groups, which are available for reaction with a suitable functional group on a toxin. Additionally, or alternatively, the antibody or toxin can be derivatized to expose or attach additional reactive functional groups. The derivatization may involve attachment of any of a number of linker molecules such as those available from Pierce Chemical Company, Rockford Ill.

A bifunctional linker having one functional group reactive with a group on the toxin, and another group reactive with an antibody, can be used to form a desired immunoconjugate. Alternatively, derivatization may involve chemical treatment of the toxin or antibody, e.g., glycol cleavage of the sugar moiety of a glycoprotein antibody with periodate to generate free aldehyde groups. The free aldehyde groups on the antibody may be reacted with free amine or hydrazine groups on the toxin to bind the toxin thereto. (See U.S. Pat. No. 4,671,958). Procedures for generation of free sulfhydryl groups on antibodies or antibody fragments, are also known (See U.S. Pat. No. 4,659,839).

Many procedures and linker molecules for attachment of various compounds including toxins are known. See, for example, European Patent Application No. 188,256; U.S. Pat. Nos. 4,671,958, 4,659,839, 4,414,148, 4,699,784; 4,680,338; 4,569,789; 4,589,071; and Borlinghaus et al. *Cancer Res.* 47: 4071–4075 (1987), which are incorporated herein by reference. In particular, production of various immunotoxin conjugates is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann, *Science,* 252: 1657 (1991), U.S. Pat. Nos. 4,545,985 and 4,894,443 which are incorporated herein by reference. See also, e.g., Birch and Lennox, *Monoclonal Antibodies: Principles and Applications*, Chapter 4, Wiley-Liss, New York, N.Y. (1995); U.S. Pat. Nos. 5,218,112, 5,090,914; Hermanson, *Bioconjugate Techniques*, Academic Press, San Diego, Calif. (1996). In preferred embodiments, the linker molecule is m-Malimidobenzoyl-N-hydroxysuccinimideester (MBS) which can be used to prepare immunotoxin conjugates as described, for example, in Youle and Nevelle, *Proc. Natl. Acad. Sci.,* 77(9):5483–5486 (1980).

In some circumstances, it is desirable to free the toxin from the antibody when the immunotoxic conjugate has reached its target site. Therefore, immunotoxic conjugates comprising linkages which are cleavable in the vicinity or within the target site may be used when the toxin is to be released at the target site. Cleaving of the linkage to release the agent from the ligand may be prompted by enzymatic activity or conditions to which the immunoconjugate is subjected either inside the target cell or in the vicinity of the target site. A number of different cleavable linkers are known to those of skill in the art. See U.S. Pat. Nos. 4,618,492; 4,542,225, and 4,625,014. SPDP is a reversible NHS-ester, pyridyl disulfide cross-linker used to conjugate amine-containing molecules to sulfhydryls. Another chemical modification reagent is 2-iminothiolane which reacts with amines and yields a sulfhydryl. Water soluble SPDP analogs, such as Sulfo-LC-SPDP (Pierce, Rockford, Ill.) are also available. SMPT is a reversible NHS-ester, pyridyl disulfide cross-linker developed to avoid cleavage in vivo prior to reaching the antigenic target. Additionally, the NHS-ester of SMPT is relatively stable in aqueous solutions.

Pharmaceutical Compositions and Method of Administration

Immunotoxic conjugates of the present invention are useful for the treatment of focal muscle spasms such as, but not limited to, blepharospasm, cervical dystonia, hand dystonia, limb dystonia, hemifacial spasm, bruxism, strabismus, VI nerve palsy, spasmodic dysphonia, and oromandibular dystonia. In preferred embodiments, the immunotoxin conjugate comprises ricin ($RCA_{60}$). While not bound by theory, it is believed that the use of the galactose binding ricin B-chain helps prevent diffusion of the immunotoxin from the site of administration. Additionally, the B-chain increases the potency of the ricin A-chain toxin.

The formulations containing therapeutically effective amounts of the immunotoxin conjugates of the present invention are either sterile liquid solutions, liquid suspensions or lyophilized versions and optionally contain stabilizers or excipients. Lyophilized compositions are reconstituted with suitable diluents, e.g., water for injection, saline, 0.3% glycine and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, and the like. Actual methods for preparing administrable compositions will be known or apparent to those skilled in the art and are described in more detail in such publications as *Remington's Pharmaceutical Science*, 19th ed., Mack Publishing Company, Easton, Pa. (1995).

The compositions for administration will commonly comprise a solution of the immunotoxin conjugate of the present invention dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques.

As will be readily understood by the clinician of ordinary skill in the art, the dose will be dependent upon the properties of the particular immunotoxin conjugate employed, e.g., its activity and biological half-life, the concentration of immunotoxin conjugate in the formulation, the site and rate of dosage, the clinical tolerance of the patient involved, the disease afflicting the patient, the severity of the disease, and the like.

Preferably, the pharmaceutical compositions containing the immunotoxin conjugates will be administered by intramuscular injection in a therapeutically effective dose ranging from about 1 ng to 200 ng depending upon the size of the muscle, the severity of the focal muscle spasm, and the specificity and toxicity of the conjugate. For example, for a ricin-anti-nAchR immunotoxin conjugate, an eye muscle will typically require between 5 and 20 ng of conjugate, and a vocal chord will generally require 1 to 2 ng. Preferably, the dose is administered at the site of the neuromuscular junctions of the muscle which is being treated. Those of skill will understand that the dose may be administered to the various neuromuscular junctions of the muscle whose activity one wishes to diminish, this being particularly preferred for muscles whose size allows for such a mode of administration. Therapeutically effective amounts of immunotoxin conjugates of the present invention can be administered alone, in combination, or in conjunction with therapeutically effective amounts of the unconjugated forms of the toxins (e.g., botulinum toxin).

Preferably, the dosage is administered once but may be applied periodically until either a therapeutic result is achieved or until side effects warrant discontinuation of therapy. Generally, the dose should be sufficient to treat or ameliorate symptoms or signs of focal muscle spasm without producing unacceptable toxicity to the patient. An effective amount of the compound is that which provides either subjective relief of a symptom(s) or an objectively identifiable improvement as noted by the clinician or other qualified observer.

Solutions comprising immunotoxin conjugates of the present invention will typically have a pH in the range of pH 5 to 9.5, preferably pH 6.5 to 7.5. The immunotoxin conjugates should be in a solution having a suitable pharmaceutically acceptable buffer such as phosphate, tris (hydroxymethyl) aminomethane-HCl, saline, or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine can also be included to a solution comprising the immunotoxin conjugate of the present invention. In preferred embodiments the buffer is a saline solution of 0.9% comprising human serum albumin of 1 mg/ml. Antibody or immunotoxin may also be administered via microspheres, liposomes or other microparticulate delivery systems placed in certain tissues including blood.

Although the present invention has been described in some detail by way of illustration and example for purposes of clarity of understanding, it will be obvious that certain changes and modifications may be practiced within the scope of the appended claims.

EXAMPLE 1

ITX Cytotoxic Activity

A. Protein Purification

Ricin was purified from seeds of *Ricinus communis* by elution from Sepharose columns with N-acetylgalactosamine, as described by Nicolson et al. (*Biochemistry* (1974) 13:196–204). Onconase was purified from the eggs of *Rana pipiens*, as described previously (Ardelt et al., *J. Biol. Chem.*, (1991) 266:245–251). CRM 107 (a mutated form of diphtheria toxin with an inactivated binding domain) was purified as described previously (Greenfield L, Johnson V G, Youle R J, *Science,* 1987; 238:536–539). The plant lectin, $RCA_{120}$, was purchased from Sigma (St. Louis, Mo.). MoAb 35 (an anti-nicotinic acetylcholine receptor monoclonal antibody) (Tzartos et al., *J. Biol. Chem.*, (1981) 256:8635–8645; Clementi and Sher, *Eur. J. Cell Biol.*, (1985) 37:220–228; Tzartos et al., *Proc. Natl. Acad. Sci. USA,* 1982; 79:188–192) was purified from ascites (mouse) by ammonium sulfate precipitation and DEAE sepharose.

B. Immunotoxin Synthesis

Conjugation of transferrin (tfn) with CRM 107 was accomplished as described previously (Johnson V G, Wilson D, Greenfield L, Youle R J., *J. Biol. Chem.* (1988) 263: 1295–1300). Conjugation of MoAb 35 to ricin was performed as described previously (Youle and Neville, *Proc.*

*Natl. Acad. Sci. USA* (1980) 77:5483–5486), with the following modifications. The antibody was prepared by adding 71 µl of 1 M dithiothreitol (DTT) in phosphate-buffered saline (PBS) to 2.8 mg (in 0.5 ml) of antibody. This mixture was incubated for 30 minutes in order to partially reduce the antibody. The antibody-DTT mixture was then applied to a G-25, PD-10 gel filtration column equilibrated with PBS. Peak antibody fractions were pooled. Ricin, 10 mg in 1.4 ml of PBS was mixed with 39 µl of dimethylformamide containing 0.15 mg of the bifunctional cross-linking agent, m-maleimidobenzoyl-N-hydroxysuccinimidyl (MBS) ester (Pierce Chemical Co.). The mixture was incubated at room temperature for 30 minutes. Ricin-MBS was immediately reacted with freshly reduced antibody and incubated at 4° C. overnight.

C. Immunotoxin Purification

The conjugate was separated from unreacted ricin by HPLC on a TSK 3000 SW column (size exclusion) in 0.1 M sodium phosphate buffer (pH 7.4). The peak fractions from several runs containing both unreacted antibody and immunotoxin were pooled and loaded onto an immobilized D-galactose affinity column (Pierce) at 4° C. After the column was flushed with PBS to remove unreacted antibody, 0.1 M lactose was run over the column to elute the purified immunotoxin.

D. Tissue Culture

The C2 mouse skeletal muscle cells (Yaffe and Saxel, *Nature* (1977) 270:725–727; Inestrosa et al., *Exp. Cell. Res.* (1983) 147:393–405) were maintained as exponentially growing myoblasts in medium consisting of Dulbecco's modified Eagle medium with high glucose, supplemented with 0.5% chick embryo extract, 20% fetal bovine serum, 0.2 M L-glutamine, and 100 µg/ml of penicillin-streptomycin. The cells were grown in 100 mm sterile Corning culture dishes under humidified 95% air/5% $CO_2$ atmosphere at 37° C. Cell stocks were maintained until reaching 70–80% confluence and then harvested with trypsin and replated. Both the human rhabdomyosarcoma (RD) (Syapin et al., *Brain Research*, (1982) 231:365–377; Sine, *J. Biol. Chem.*, (1988) 34:18052–18062; Luther et al., *The Journal of Neuroscience*, (1989) 9:1082–1096) and human glioblastoma multiforme (U251) cell lines were maintained in Dulbecco's modified Eagle medium supplemented with 10% fetal calf serum, 1% L-glutamine, non-essential amino acids, 0.5% sodium pyruvate, and 0.1% gentamycin. Cells were grown in 100 mm Corning culture dishes. The cells were harvested with trypsin and replated upon reaching 50–60% confluence.

E. Cellular Protein Synthesis Assays

Inhibition of protein synthesis was used to assay the cytotoxic effect of ITX, ricin, $RCA_{120}$, Tfn-CRM 107, and onconase in C2 myoblasts, myotubes, RD, and U251 cells by methods similar to those described by Zovickian, et al (*J. Neurosurg.*, (1987) 66:850–861). Cells were plated into 96-well microwell plates at a density of $5 \times 10^5$/ml in 100 µl of media and incubated overnight. Fresh media was added to each well prior to the addition of either serially diluted toxins and/or 0.1 M lactose or PBS. Cells were then incubated 18–20 hours and the growth media was aspirated and replaced with leucine-free RPMI media and 0.1 µCi of ($^{14}$C)-labeled leucine. After 2 hours cells were harvested onto glass fiber filters with a PHD cell harvester. All cytotoxicity assays were performed 2–5 times in triplicate. Results were expressed as the percentage of incorporation of radioactivity compared to either lactose or PBS controls.

Cytotoxicity assays on myotubes were performed as described above with slight modifications. After myoblasts reached 80–90% confluence in the wells, growth media was removed and replaced with Dulbecco's modified Eagle medium supplemented with 10% horse serum (fusion medium). Every 24 hours, the fusion medium was replaced. After 72 hours in fusion medium myotube acetylcholine receptor expression is at its maximum (Inestrosa et al., *Exp. Cell Res.* (1983) 147:393–405) and cells were used in cytotoxicity assays.

F. ITX Cytotoxicity

The potency and specificity of ITX was first examined by comparing activity on C2 muscle cells in undifferentiated and differentiated states. With decreased serum and withdrawal of chicken embryo extract, nearly confluent myoblasts which express undetectable levels of nicotinic acetylcholine receptors are induced to form multi-nucleated myotubes (Inestrosa et al., *Exp. Cell Res.*, (1983) 147:393–405). The myotubes often contracted in the culture dish after 3 days and reportedly express high densities of nicotinic acetylcholine receptor clusters. Id.

Toxicity of ricin and ITX to C2 myotubes and myoblasts in the presence and absence of 0.1 M lactose was measured. The assays demonstrate a steep dose-response inhibition of protein synthesis. Myotube protein synthesis was inhibited 50% ($IC_{50}$) at an ITX concentration of $2.5 \times 10^{-12}$ M and at a ricin concentration of $4.5 \times 10^{-11}$ M. Lactose, a competitive inhibitor of ricin binding to cells (Olsnes et al., *Nature* (1974) 249:627–631), blocked ricin toxicity 800-fold, whereas ITX was barely inhibited by lactose (1.4-fold), indicating that ITX was binding and inhibiting protein synthesis, not via the ricin receptor but via the nicotinic acetylcholine receptor. Myotubes were more sensitive to ITX than ricin, and in the presence of lactose, myotubes were 20,000-fold more sensitive to ITX ($3.5 \times 10^{-12}$ M) than native ricin ($7 \times 10^{-8}$ M).

To corroborate the nicotinic acetylcholine receptor specificity of ITX, ricin and ITX activity on C2 myoblasts (nicotinic acetylcholine receptor-negative) was examined. Myotubes, were 100-fold more sensitive to ITX than myoblasts. However, ricin toxicity was essentially identical for both cell types. In the presence of lactose, myotubes (nicotinic acetylcholine receptor-positive) were over 14,000-fold more sensitive to ITX than were myoblasts (nicotinic acetylcholine receptor-negative), whereas ricin was actually less toxic to myotubes than myoblasts.

The cytotoxic properties of ITX and ricin on two human neoplastic cell lines was also compared. RD cells, human rhabdomyosarcoma cells, are known to express functional human nicotinic acetylcholine receptors (Syapin et al, *Brain Research* (1982) 231:365–377; Sine, *J. Biol. Chem.* (1988) 34:18052–18062; Luther et al., *The Journal of Neuroscience* (1989) 9:1082–1096) whereas U251 cells, of human glioma origin are not. ITX had a nearly identical dose-response toxicity profile on RD cells as seen with myotubes with an $IC_{50}$ of $2.4 \times 10^{-12}$ M. Addition of lactose decreased ITX activity only 1.4-fold but inhibited toxicity of ricin 100-fold. When ricin binding is blocked with lactose, RD cells are greater than 1000-fold more sensitive to ITX than ricin alone. On U251 cells ITX had an $IC_{50}$ of $2.5 \times 10^{-10}$ M, about 100-fold higher than the nicotinic acetylcholine receptor positive RD cells, whereas ricin was equally toxic to RD and U251 cells. Thus, non-nicotinic acetylcholine receptor expressing cell lines (myoblasts and U251 cells) in the presence of lactose were between 14,000–21,000-fold less sensitive to ITX than were the nicotinic acetylcholine receptor expressing cell lines (myotubes and RD cells).

EXAMPLE 2

Cytotoxic Activity of Other Protein Toxins

In an effort to identify the most potent and specific reagent, three other toxins: RCA120, Tfn-CRM 107, and onconase were investigated. $RCA_{120}$ (MW=120,000) is a tetrameric plant lectin similar to a dimer of ricin (Lin and Li, *Eur. J. Biochem.* (1980) 105:453–459). Myotubes and myoblasts were nearly equally sensitive to $RCA_{120}$ ($IC_{50}$=3.5× $10^{-10}$ M). Tfn-CRM 107 (MW=150,000) is an immunotoxin (Johnson et al., *J. Neurosurg.* (1989) 70:240–248) selective for the transferrin receptor and high transferrin receptor numbers on myotube cell cultures and high rates of iron uptake (Sorokin et al., *J. Cell Physiol.* (1987) 131:342–353) have been observed. Tfn-CRM 107 was nearly as toxic to myotubes ($IC_{50}$=3×$10^{-7}$ M) as myoblasts ($IC_{50}$=2×$10^{-7}$ M). However, overall myotoxicity was lower than predicted. Onconase (MW=12,000), currently in phase III clinical trials for treatment of pancreatic cancer, was 2.5-fold more toxic to myotubes than myoblasts at the $IC_{50}$ (2×$10^{-6}$ M and 8×$10^{-7}$ M, respectively); however, it was the least toxic to myotubes of all the proteins examined. Only ITX demonstrated significant differential toxicity between myotubes and myoblasts.

EXAMPLE 3

Rat Muscle Biopsies

Female Balb/c mice (16–18 g) received 0.3 ml IP injections (30 g needle). For each agent, five serial 2-fold dilutions of toxin were tested. At each dilution three mice were injected and the experiment was repeated twice. The maximum tolerated dose was determined to be the maximum dose/kg where all animals survived. This dose was used as an estimate of the maximum tolerated dose (MTD) in rats. The maximum tolerated dose of ITX was 2 μg/kg in mice. Thus, for 250 g rats 1/100 and 1/300 of the maximum tolerated dose of ITX was estimated to be 5 ng and 1.7 ng, respectively. These doses of ITX were delivered intramuscularly to the rats in a volume of 30 μl. Hereafter in this example, comparable doses of the toxins refers to doses that are the same fraction of the maximum tolerated dose (or $LD_{50}$ in the case of BTX). This comparison yields an estimate of the therapeutic window, which may be a useful gauge of the toxins clinical potential.

Frozen and lyophilized BTX (Allergan) was reconstituted and diluted in 1.2 ml of sterile PBS to a final concentration of 83 U/ml and immediately used for injections. Thirty microliters of BTX containing either 0.25 U (0.1 ng) or 2.5 U (1 ng) was injected into the rat gastrocnemius. These doses correspond to 1/100 and 1/10 of the reported rat $LD_{50}$, respectively (Burgen et al., *J. Physiol.*, (1949) 109:10–24). BTX was not diluted in blue dextran.

Female Sprague-Dawley rats (225–250 g) from Taconic farms were anesthetized with ketamine/xylazine (0.1 cc/100 g) IP and the leg to be injected was immobilized, shaved, and sterilized with betadine. The midbelly of the gastrocnemius was exposed by microdissection and five-fold dilutions of toxin or PBS prepared in 25 mg/ml blue dextran were unilaterally injected with a 30 g needle. To insure reproducible depth of injection, a plastic stopper was slipped over the needle such that 3.5 mm of the needle remained exposed. The needle was inserted so the muscle was flush against the plastic stopper. Toxins were injected from a syringe pump (KD Scientific) at a rate of 1.0 μl/min for 30 minutes (total volume=30 μl). After the infusions were completed, the skin was sutured closed. The gastrocnemius muscles were biopsied seven days after treatment at the site of blue dextran staining of the muscle. Muscle specimens were fresh-frozen in isopentane and cooled in liquid nitrogen. Serial sections were stained with hematoxylin-eosin (H & E) or modified Gomori trichrome and examined by light microscopy in a blinded fashion.

Muscle biopsy from the ITX-injected site seven days after treatment demonstrated a severe inflammatory response in the endomysial parenchyma and the perimysium. Inflammatory cells were invading muscle fibers in a pattern identical to that seen in primary inflammatory myopathy (Dalakas M C, *N. Engl. J. Med.* (1991) 325:1487–1498). Necrosis, phagocytosis, and separation of the muscle fibers, probably due to edematous changes in the interstitial tissue, were prominent. Inflammation and muscle fiber destruction was prominent at the site of injection. Areas of specimen remote from the injection site (beyond 2–3 mm) had minimal changes. Control-injected (blue dextran diluted in PBS) rats showed no or minimal response consisting of scattered inflammatory cells and mild edematous change limited to the perimysium. No primary invasion by inflammatory cells or destruction of muscle fibers was detected in the control rats.

Evidence of muscle weakening by ITX was observable at a dose 1/300 of the maximum tolerated dose. Muscle weakness induced by Tfn-CRM 107 and $RCA_{120}$ (Example 2) was only noticeable at doses near their maximum tolerated dose, and onconase had no apparent effect. Histopathological evidence of muscle fiber damage correlated with observable muscle weakness (Example 4). ITX at a dose 1/300 of the maximum tolerated dose exerted a significant, selective and focal destruction to the muscle as assessed histologically seven days after injection, whereas ricin alone showed nearly undetectable fiber damage at a dose 1/16 of its maximum tolerated dose. This indicates that the monoclonal antibody to the nicotinic acetylcholine receptor is indeed binding ITX specifically to the muscle.

EXAMPLE 4

Muscle Strength Assessment

The efficacy of BTX has been correlated with its muscle weakening effects. Since no good animal model exists for focal muscle spasm, a muscle strength test using the rotorod was adapted to compare ITX to BTX. The rotorod is a preprogrammable, rotating cylinder suspended 1.5 feet above a plastic platform used for quantitative measurement of rat motor performance (Janicke et al., *Ann. N.Y. Acad. Sci.* (1988) 515:97–107). Rats were trained to run on the rotorod daily. The rotorod was programmed to accelerate to the desired speed in 10 seconds. The rats were considered to be successfully trained on the rotorod for the first experiment when they were able to complete the task (25 rpm for 180 seconds) on three consecutive days. In the second experiment rats were trained until they were able to complete the task at 30 rpm for 180 seconds.

Immediately prior to injections, all rats ran on the rotorod and were able to complete the training run (25 rpm for 180 s for the first experiment and 30-rpm for the second rotorod experiment.). In the first rotorod experiment, rats were randomly assigned to three groups and injected with either BTX at 1/100 (n=6) of the $LD_{50}$ or ITX (n=6) at a dose 1/100 of the maximum tolerated dose, or PBS (n=6). In the second rotorod experiment there were six groups: BTX at 1/10 and 1/100 of the $LD_{50}$, ITX at 1/100 and 1/300 of the maximum tolerated dose, unconjugated MoAb 35 at a concentration used in the conjugation of ITX at 1/100 of the maximum tolerated dose, and PBS. All groups in the second rotorod experiment contained four rats. Unconjugated ricin at the concentration used in ITX was lethal to the rats and therefore was unable to be used as a control. Following injection all rats were tested in three 180-s trials at 30 rpm and times prior to falling were averaged for each rat. The time spent on the bar before falling for the six rats per group in the first rotorod experiment and four rats per group in the second rotorod experiment was averaged and recorded as data points.

Figure 1:
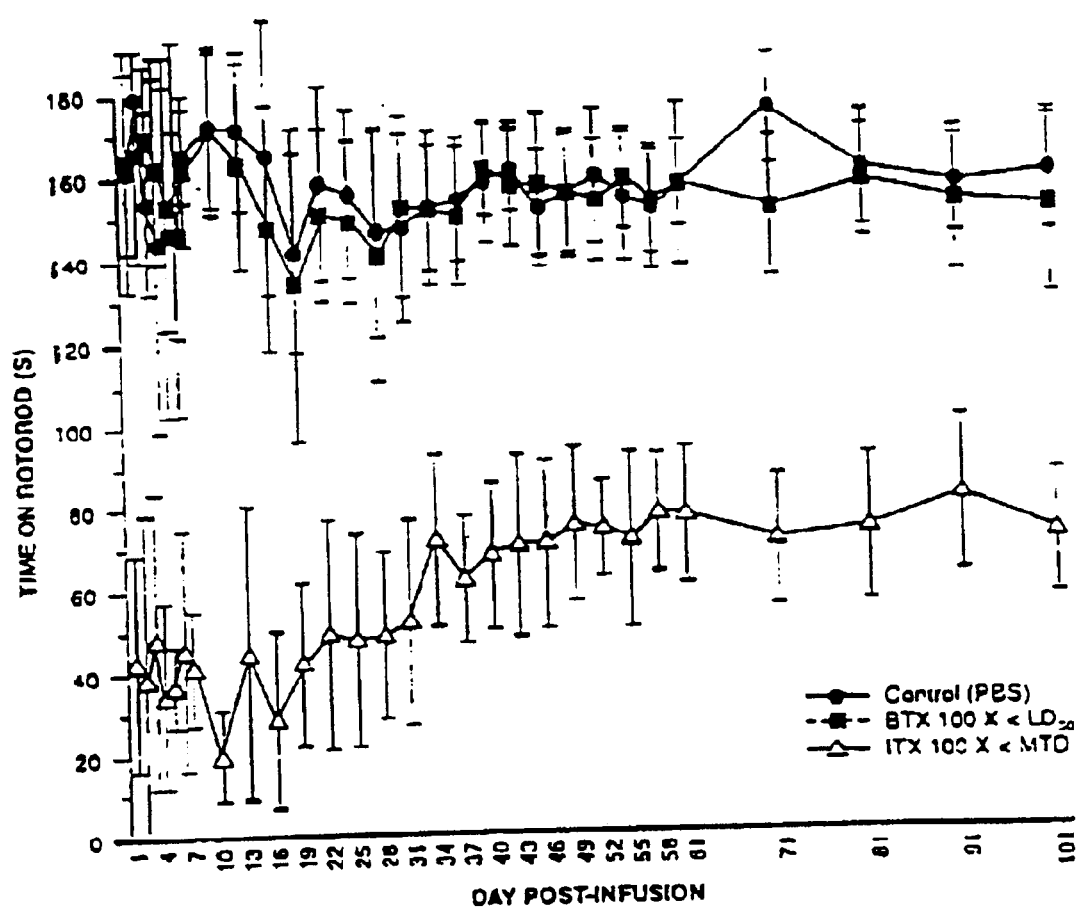
Figure 2:
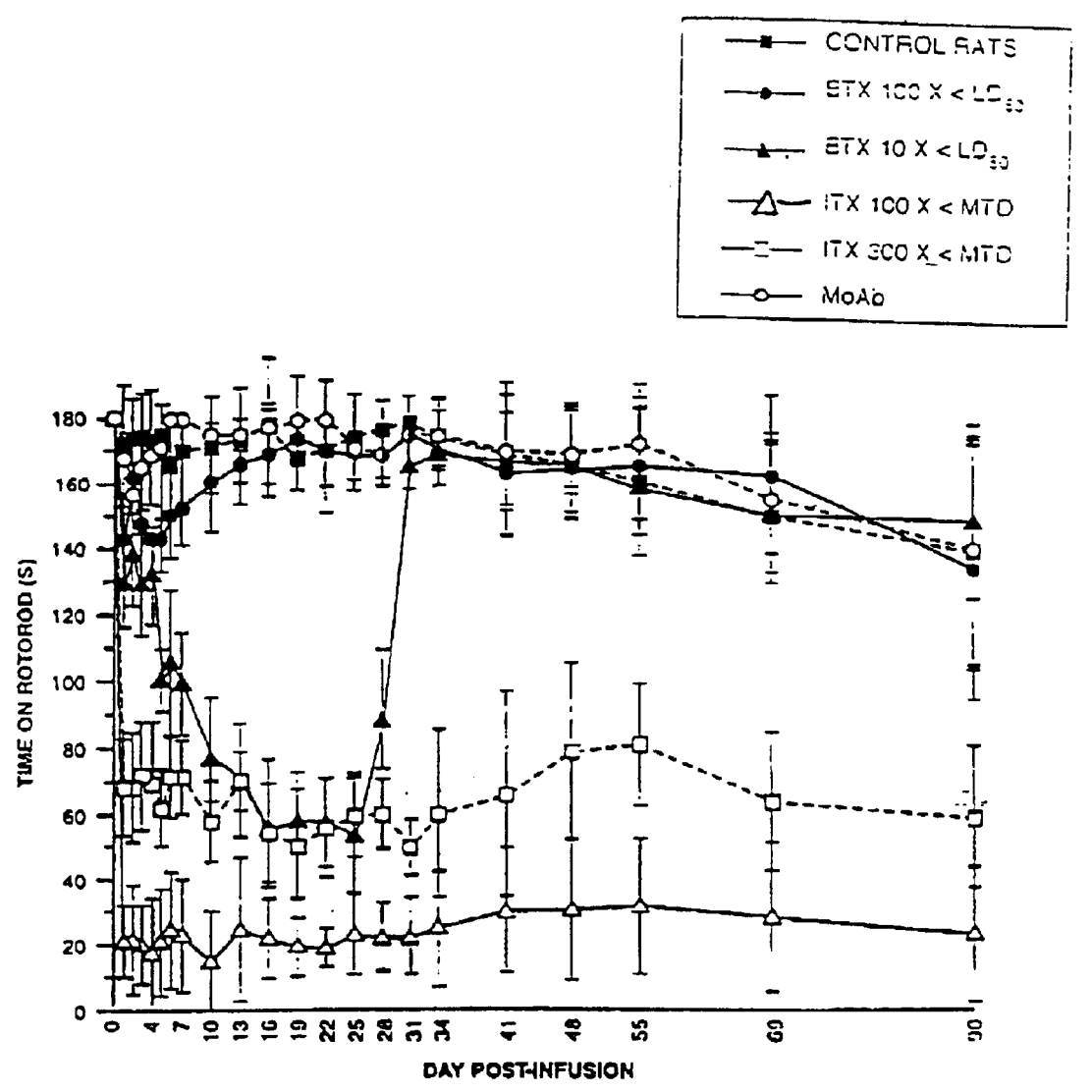

ITX and BTX were compared in two independent experiments (FIGS. 1, 2) evaluating the performance of rats on the rotorod test as a function of time after injection with toxins. The effect of extremely low doses of ITX were quick, dramatic and sustained, while comparable doses of BTX were minimal and transient. After one day, rats injected with ITX at 1/100 of the maximum tolerated dose showed sufficient weakening such that the rats were only able to run for an average of 42 s in the first rotorod experiment (FIG. 1) and 20 s in the second rotorod experiment (FIG. 2). By comparison, control rats ran for an average of 162 s and 172 s in the first and second rotorod experiments, respectively. Rats treated with ITX at a dose 1/300 of the maximum tolerated dose in the second rotorod experiment (FIG. 2) have maintained running times between 50–80 s. BTX, at 1/100 of the $LD_{50}$, did not affect strength significantly compared to saline injected rats in either experiment. Rats treated with BTX at a dose 1/10 of the $LD_{50}$ in the second rotorod experiment became observably weak in the injected limb correlating with their diminished running times on the rotorod. However, after 4–5 weeks these rats regained strength as their rotorod times returned to control values. This data confirms the result of a pilot trial of BTX injected rats at 1/10 of the $LD_{50}$ where performance on the rotorod returned to control values by 6 weeks. In contrast, ITX treated rats have maintained running times far less than either BTX or control treated rats throughout the duration of the experimental period. Observation of rats on the rotorod showed that both ITX and BTX treated limbs lagged behind the three untreated limbs as the rats began to fatigue. This was another indication that weakness had been induced in both ITX and BTX treated rats. Further, it appeared that the weakness was only in the injected limb. Rats treated with saline, BTX at 1/100 of the $LD_{50}$, and unconjugated MoAb 35 showed no observable limb weakening effects while running on the rotorod. All rats gained weight, demonstrated normal grooming practices and were alert when startled, further indicating the absence of severe systemic toxicity.

To perform on the rotorod, it is necessary to coordinate movement and accelerate for the initial ten seconds of the task in order to achieve the top rate of 30 rpm. The fact that all rats were able to overcome the initiation and acceleration phase on the rotorod demonstrates that generalized motor function was not impaired and the decreased running times on the rotorod reflect peripheral, not central, effects of the toxins (BTX and ITX).

When BTX and ITX were examined on the rotorod at comparable doses (1/100 of the $LD_{50}$ and 1/100 of the maximum tolerated dose, respectively), the ITX-injected animals demonstrated focal muscle weakness while the BTX-injected animals were unaffected. When the dose of BTX was increased to 1/10 of the $LD_{50}$ a significant weakness appeared but it only lasted for 4–5 weeks. This result is consistent with leg twitch studies performed by Holds et al on the rat gastrocnemius muscle after a single injection of 1.0 U of botulinum toxin in which muscle strength returned to near pre-injection values between 4–6 weeks (Holds et al., Opthalmic Plast. Reconstructr. Surg. (1990) 6:252–259). Therefore, based on the rotorod results, ITX appears to be thirty times more potent than BTX and yields a dramatically longer response. The results demonstrate that ITX has excellent potential for a safe and long lasting focal muscle weakness and may have clinical applications in the treatment of patients refractory to BTX used alone, in combination, or even in place of BTX.

All publications and patents mentioned in this specification are herein incorporated by reference into the specification to the same extent as if each, individual publication or patent was specifically and individually indicated to be incorporated herein by reference.

What is claimed is:

1. A method of treating a focal muscle spasm, comprising administering, by intramuscular injection, a therapeutically effective dose of an immunotoxin conjugate to a muscle of said focal muscle spasm, wherein said immunotoxin conjugate comprises an antibody conjugated to a cellular toxin selected from the group consisting of: ricin and abrin, wherein said antibody is selectively reactive, under immunologically reactive conditions, to a nicotinic acetylcholine receptor;

wherein said antibody of said immunotoxin conjugate binds to a nicotinic acetylcholine receptor of a muscle cell of said muscle, and said cellular toxin of said immunotoxin conjugate mediates the death of said muscle cell.

2. The method of claim 1, wherein the antibody is a monoclonal antibody.

3. The method of claim 1, wherein said mammalian acetylcholine receptor is a human acetylcholine receptor.

4. The method of claim 1, wherein said muscle toxin is ricin.

5. The method of claim 1, wherein the focal muscle spasm is selected from the group consisting of: blepharospasm, cervical dystonia, hand dystonia, limb dystonia, hemifacial spasm, bruxism, strabismus, VI nerve palsy, spasmodic dysphonia, and oromandibular dystonia.

6. A method of treating a focal muscle spasm, comprising administering, by intramuscular injection, a therapeutically effective dose of an immunotoxin conjugate to a muscle of said focal muscle spasm, wherein said immunotoxin conjugate comprises an antibody conjugated to a galactose binding moiety and a cellular toxin selected from the group consisting of: ricin-A and abrin-A, wherein said antibody is selectively reactive, under immunologically reactive conditions, to a nicotinic acetylcholine receptor;

wherein said antibody of said immunotoxin conjugate binds to a nicotinic acetylcholine receptor of a muscle cell of said muscle, and said cellular toxin of said immunotoxin conjugate mediates the death of said muscle cell.

7. The method of claim 6, wherein said galactose binding moiety is selected from the group consisting of: ricin-B and abrin-B.

8. The method of claim 6, wherein the antibody is a monoclonal antibody.

9. The method of claim 6, wherein said mammalian acetylcholine receptor is a human acetylcholine receptor.

10. The method of claim 6, wherein said toxin is ricin.

11. The method of claim 6, wherein the focal muscle spasm is selected from the group consisting of; blepharospasm, cervical dystonia, hand dystonia, limb dystonia, hemifacial spasm, bruxism, strabismus, VI nerve palsy, spasmodic dysphonia, and oromandibular dystonia.

* * * * *